US009504474B2

(12) United States Patent
Chen et al.

(10) Patent No.: US 9,504,474 B2
(45) Date of Patent: Nov. 29, 2016

(54) VASO-OCCLUSIVE DEVICES WITH IN-SITU STIFFENING

(75) Inventors: Hancun Chen, San Ramon, CA (US); Richard Murphy, Sunnyvale, CA (US)

(73) Assignees: Stryker Corporation, Kalamazoo, MI (US); Stryker European Holdings I, LLC, Kalamazoo, MI (US)

(*) Notice: Subject to any disclaimer, the term of this patent is extended or adjusted under 35 U.S.C. 154(b) by 789 days.

(21) Appl. No.: 13/466,393

(22) Filed: May 8, 2012

(65) Prior Publication Data

US 2012/0303053 A1  Nov. 29, 2012

Related U.S. Application Data

(60) Provisional application No. 61/489,160, filed on May 23, 2011.

(51) Int. Cl.
*A61M 29/00* (2006.01)
*A61B 17/12* (2006.01)
*A61B 17/00* (2006.01)

(52) U.S. Cl.
CPC ...... *A61B 17/12113* (2013.01); *A61B 17/1214* (2013.01); *A61B 17/1219* (2013.01); *A61B 2017/00867* (2013.01)

(58) Field of Classification Search
CPC ............ A61B 17/12113; A61B 17/1214; A61B 17/1219; A61B 2017/00867
USPC .......... 606/151, 200; 623/1.15; 424/422
See application file for complete search history.

(56) References Cited

U.S. PATENT DOCUMENTS 4,994,069 A     2/1991  Ritchart et al.
5,373,619 A *  12/1994  Fleischhacker et al. ....... 29/451
(Continued)

OTHER PUBLICATIONS

Prosecution History from U.S. Appl. No. 10/695,151, including (144 pages total): Pre-Brief Conference Decision dated Jun. 5, 2009; Pre-Brief Conference Request in response to Final Office Action dated Mar. 10, 2009, response submitted Apr. 15, 2009; Final Office Action mailed Mar. 10, 2009; Amendment response to non-final office action dated Aug. 7, 2008, response submitted on Nov. 7, 2008; Non-final office action dated Aug. 7, 2008; Pre-Brief Conference Decision dated May 21, 2008; Pre-Brief Conference Request in response to Final Office Action dated Dec. 11, 2007, response submitted Mar. 11, 2008; Final Office Action dated Dec. 11, 2007; Amendment response to non-final office action dated Jun. 28, 2007, response submitted on Sep. 26, 2007; Non-final office action dated Jun. 28, 2007; Amendment submitted in response in Final office action dated Jan. 9, 2007, response submitted Apr. 27, 2007 Final office action dated Jan. 9, 2007; Amendment response to Non-final office action dated Jul. 13, 2006, response submitted Nov. 2, 2006 Non-final office action dated Jul. 13, 2006.

(Continued)

*Primary Examiner* — Julie A Szpira
(74) *Attorney, Agent, or Firm* — Vista IP Law Group, LLP (57) ABSTRACT

A vaso-occlusive device includes a first coil made from a first substantially non-expansile material, and a second coil at least partially co-wound with the first coil and made from a second expansile material. The second coil has a contracted state and an expanded state, in which the second coil expands radially and/or longitudinally. The vaso-occlusive device has increased stiffness when the second coil is in its expanded state.

20 Claims, 6 Drawing Sheets

(56) References Cited

U.S. PATENT DOCUMENTS

| | | | |
|---|---|---|---|
| 5,718,711 A * | 2/1998 | Berenstein et al. | 606/191 |
| 6,004,338 A * | 12/1999 | Ken et al. | 606/191 |
| 6,616,617 B1 | 9/2003 | Ferrera et al. | |
| 6,723,108 B1 | 4/2004 | Jones et al. | |
| 7,645,292 B2 | 1/2010 | Porter | |
| 2002/0169473 A1 | 11/2002 | Sepetka et al. | |
| 2004/0002733 A1 | 1/2004 | Teoh | |
| 2004/0006362 A1 * | 1/2004 | Schaefer et al. | 606/200 |
| 2004/0098028 A1 | 5/2004 | Martinez | |
| 2005/0021074 A1 | 1/2005 | Elliott | |
| 2005/0090861 A1 | 4/2005 | Porter | |
| 2005/0149109 A1 | 7/2005 | Wallace et al. | |
| 2005/0171572 A1 * | 8/2005 | Martinez | 606/200 |
| 2005/0209633 A1 | 9/2005 | Callister et al. | |
| 2005/0267510 A1 | 12/2005 | Razack | |
| 2006/0079926 A1 * | 4/2006 | Desai et al. | 606/200 |
| 2007/0078479 A1 | 4/2007 | Belenkaya et al. | |
| 2007/0239194 A1 | 10/2007 | Tran et al. | |
| 2007/0299464 A1 | 12/2007 | Cruise et al. | |
| 2011/0245861 A1 * | 10/2011 | Chen et al. | 606/200 |

OTHER PUBLICATIONS

Prosecution History from U.S. Appl. No. 11/242,952, including (170 pages total): Non-final office action mailed Mar. 28, 2012; Amendment response to Final office action mailed Jan. 12, 2010, response submitted on Apr. 2, 2011; Final office action mailed Jan. 4, 2011; Amendment response to Non-Final office action mailed Jul. 27, 2010, reponse submitted Oct. 20, 2010 Non-final office action mailed Jul. 27, 2010; Pre-brief conference decision mailed May 28, 2010; Pre-brief conference request in response to Final office action mailed Jan. 12, 2010, reponse submitted Apr. 9, 2010; Final office action mailed Jan. 12, 2010; Amendment response to Non-final office action mailed Aug. 25, 2009, response submitted Oct. 26, 2009; Non-final office action mailed Aug. 25, 2009; Appeal Brief submitted May 18, 2009; Advisory Action mailed Mar. 9, 2009; Amendment response to Final office action mailed Jan. 22, 2009, response submitted Feb. 23, 2009; Final office action mailed Jan. 22, 2009; Amendment response to Non-final office action mailed Aug. 27, 2008, response submitted on Oct. 6, 2008; Non-final office action mailed Aug. 27, 2008; Advisory Action mailed Jun. 2, 2008; Amendment response to Final office action mailed Feb. 20, 2008, response submitted Apr. 15, 2008 Final office action mailed Feb. 20, 2008; Amendment response to Non-final office action mailed May 22, 2007, response submitted Nov. 29, 2007; Amendment response to Non-final office action mailed May 22, 2007, response submitted Aug. 23, 2007; Non-final office action mailed May 22, 2007.
PCT International Search Report and Written Opinion for PCT/US2012/036894, filed May 8, 2012, Applicant Stryker Corporation, Forms PCT/ISA/210,220 and 237 dated Jan. 17, 2013 (13 pages).

\* cited by examiner

VASO-OCCLUSIVE DEVICES WITH IN-SITU STIFFENING

RELATED APPLICATION DATA

The present application claims the benefit under 35 U.S.C. §119 to U.S. provisional patent application Ser. No. 61/489,160, filed May 23, 2011. The foregoing application is hereby incorporated by reference into the present application in its entirety.

FIELD

The field of the disclosed inventions generally relates to vaso-occlusive devices for establishing an embolus or vascular occlusion in a vessel of a human or veterinary patient. More particularly, the disclosed inventions relate to vaso-occlusive coils.

BACKGROUND

Vaso-occlusive devices or implants are used for a wide variety of reasons, including treatment of intra-vascular aneurysms. Commonly used vaso-occlusive devices include soft, helically wound coils formed by winding a platinum (or platinum alloy) wire strand about a "primary" mandrel. The coil is then wrapped around a larger, "secondary" mandrel, and heat treated to impart a secondary shape. For example, U.S. Pat. No. 4,994,069, issued to Ritchart et al., which is fully incorporated herein by reference, describes a vaso-occlusive device that assumes a linear, helical primary shape when stretched for placement through the lumen of a delivery catheter, and a folded, convoluted secondary shape when released from the delivery catheter and deposited in the vasculature.

In order to deliver the vaso-occlusive devices to a desired site in the vasculature, e.g., within an aneurysmal sac, it is well-known to first position a small profile, delivery catheter or "micro-catheter" at the site using a steerable guidewire. Typically, the distal end of the micro-catheter is provided, either by the attending physician or by the manufacturer, with a selected pre-shaped bend, e.g., 45°, 26°, "J", "S", or other bending shape, depending on the particular anatomy of the patient, so that it will stay in a desired position for releasing one or more vaso-occlusive device(s) into the aneurysm once the guidewire is withdrawn. A delivery or "pusher" wire is then passed through the micro-catheter, until a vaso-occlusive device coupled to a distal end of the delivery wire is extended out of the distal end opening of the micro-catheter and into the aneurysm. Once in the aneurysm, the vaso-occlusive devices bend to allow more efficient and complete packing. The vaso-occlusive device is then released or "detached" from the end delivery wire, and the delivery wire is withdrawn back through the catheter. Depending on the particular needs of the patient, one or more additional occlusive devices may be pushed through the catheter and released at the same site.

One well-known way to release a vaso-occlusive device from the end of the pusher wire is through the use of an electrolytically severable junction, which is a small exposed section or detachment zone located along a distal end portion of the pusher wire. The detachment zone is typically made of stainless steel and is located just proximal of the vaso-occlusive device. An electrolytically severable junction is susceptible to electrolysis and disintegrates when the pusher wire is electrically charged in the presence of an ionic solution, such as blood or other bodily fluids. Thus, once the detachment zone exits out of the catheter distal end and is exposed in the vessel blood pool of the patient, a current applied through an electrical contact to the conductive pusher wire completes an electrolytic detachment circuit with a return electrode, and the detachment zone disintegrates due to electrolysis.

A perceived problem with existing vaso-occlusive devices is that they may not have sufficient strength or stiffness to retain their shape after they are delivered into an aneurysm. When the above-mentioned vaso-occlusive devices are placed within an aneurysm, they tend to induce a formation of thrombi for occlusion of the aneurysm. However, with time and the influence of hemodynamic forces and thrombolytic processes, the delivered vaso-occlusive devices may move or change shape due to their relatively low stiffness or through the process of seeking a minimally energetic morphology. As a result, the delivered vaso-occlusive devices may move out of the position or shape in which they were originally placed. In some cases, the delivered vaso-occlusive devices may even dislodge out of the sack of an aneurysm.

SUMMARY

In one embodiment of the disclosed inventions, a vaso-occlusive device includes a first coil made from a first material, and a second coil at least partially co-wound with the first coil and made from a second material, where the first material is substantially non-expansile and the second material is expansile. The first material may be a metal, such as a metal selected from the group consisting of platinum, platinum-tungsten alloy, platinum-iridium alloy, platinum rhenium alloy, and platinum palladium alloy. The second material may be a polymer, such as a hydrogel.

Optionally, the first coil forms first coil loops and the second coil forms second coil loops. In some embodiments, the first coil loops and the second coil loops are packed together such that each loop is in contact with loops adjacent thereto. In other embodiments, spaces are disposed between at least some of the first coil loops and respective adjacent second coil loops. The first and second coils may be co-wound such that a plurality of successive, first coil loops separate an adjacent pair of second coil loops. Alternatively or additionally, the first and second coils may be co-wound such that a plurality of successive, second coil loops separate an adjacent pair of first coil loops. Also alternatively or additionally, the first and second coils may be co-wound such that a plurality of successive first coil loops are adjacent a plurality of successive second coil loops.

The second coil has a contracted state and an expanded state, in which the second coil expands radially and/or longitudinally. The vaso-occlusive device has increased stiffness when the second coil is in its expanded state. In embodiments where the second coil expands longitudinally, the vaso occlusive device also expands longitudinally. The second coil may transition from its contracted state to its expanded state when it absorbs liquid. In some embodiments, when the second coil is in its expanded state, the second coil loops compress the first coil loops. In other embodiments, the second coil defines an axial lumen, where, when the second coil is in its expanded state, the second coil loops substantially close the lumen. In other embodiments, the vaso-occlusive device also includes third and fourth coils at least partially co-wound with the first and second coils.

In an alternative embodiment, a vaso-occlusive device includes a first coil made from a first material, and a second coil at least partially co-wound with the first coil and made from a second material coated with a third material, where the first and second materials are substantially non-expansile and the third material is expansile. The second coil transitions from a contracted state to an expanded state when the third material absorbs liquid, and the vaso-occlusive device has increased stiffness when the second coil is in its expanded state.

Other and further aspects and features of embodiments of the disclosed inventions will become apparent from the ensuing detailed description in view of the accompanying figures.

BRIEF DESCRIPTION OF THE DRAWINGS

The drawings illustrate the design and utility of embodiments of the disclosed inventions, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

FIG. 2 shows the second elongate body in a contracted state. FIG. 3 shows the second elongate body in an expanded state.

DETAILED DESCRIPTION OF THE ILLUSTRATED EMBODIMENTS

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention, which is defined only by the appended claims and their equivalents. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

Figure 1:
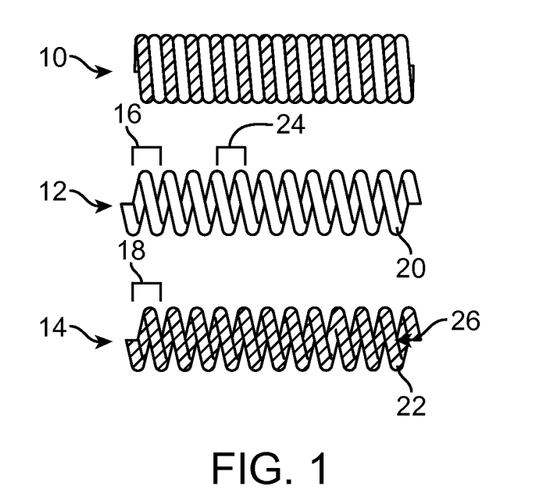
FIG. 1 is a detailed side view of a vaso-occlusive coil constructed according to one embodiment of the disclosed inventions.
Figure 2:
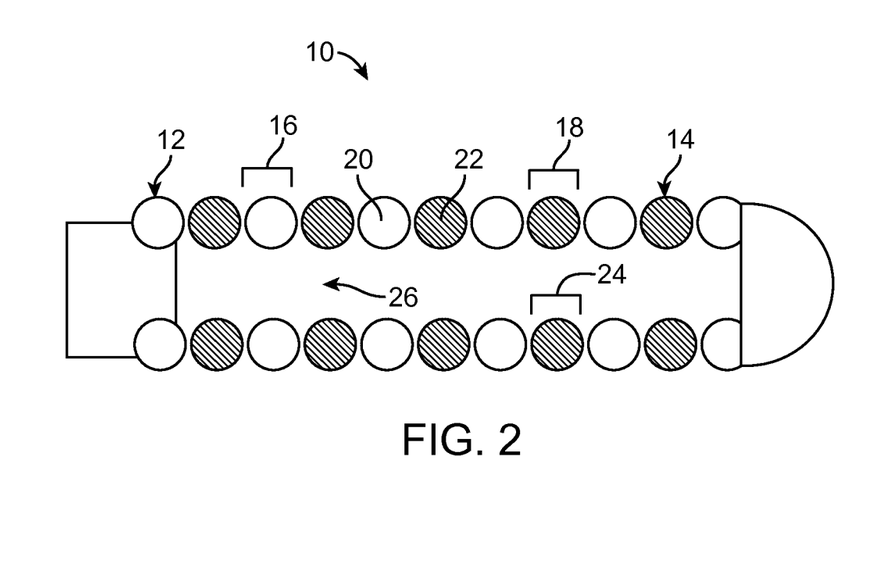
FIGS. 2 and 3 are detailed longitudinal cross-section views of the vaso-occlusive coils of FIG. 1.
Figure 3:
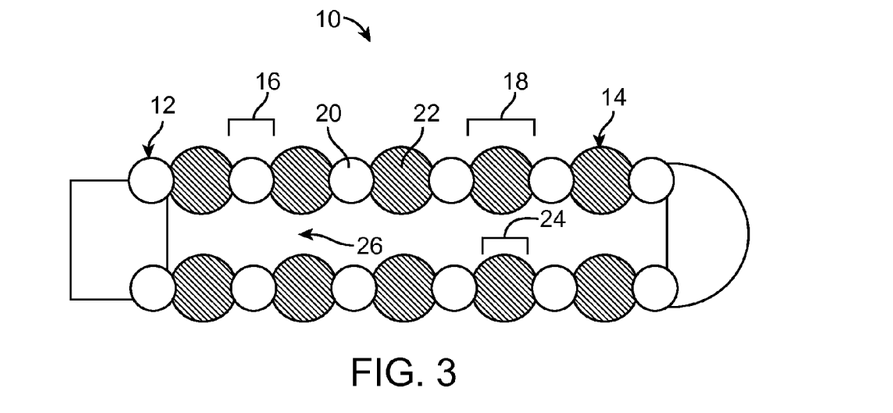

FIGS. 1-3 illustrate a vaso-occlusive coil 10 in accordance with one embodiment. The vaso-occlusive coil 10 includes a first coil 12 and a second coil 14. The first and second coils 12, 14 have a plurality of first coil loops 16 and second coil loops 18, respectively. The first and second coils 12, 14 are formed by co-winding first and second elongate bodies 20, 22, such that the first and second coil loops 16, 18 are collated together as they are formed.

The first coil 12 is made from any suitable biocompatible material that is substantially non-expansile, i.e., does not undergo more than about a 5% increase in volume under physiological conditions. For example, the first coil 12 may be made from a metal, such as pure platinum. In other embodiments, the first coil 12 may be made from an alloy, such as platinum-tungsten alloy, e.g., 8% tungsten and the remainder platinum. In further embodiments, the first coil 12 may be made from platinum-iridium alloy, platinum rhenium alloy, or platinum palladium alloy. In still other embodiments, the first coil 12 may be made from substantially non-expansile biopolymers or bio-ceramic materials.

The second coil 14 is made from any suitable biocompatible material that is expansile. For example, the second coil 14 may be made from a hydrogel, which is capable of absorbing a desired amount of aqueous fluid. Examples of hydrogels include gels formed from homopolymers, copolymers, and/or network polymers containing: polyethylene glycol, polypropylene glycol, polyvinyl alcohol, polyvinylpyrrolidone, polyacrylates, polymethacrylates, polyacrylamides, polyethyloxazoline, polysaccharides, mucopolysaccharides, polyaminoacids, carboxy alkyl celluloses, partially oxidized cellulose, hyaluronic acid, dextran, heparin sulfate, chondroitin sulfate, heparin, agar, starch, alginate, fibronectin, gelatin, collagen, fibrin, pectins, albumin, polyesters of .alpha.-hydroxy acids including polyglycolic acid, poly-DL-lactic, poly-L-lactic acid, polylactones, polyanhydrides, polyorthoesters, polydioxanone, polycaprolactones, poly(delta-valerolactone), poly(gamma-butyrolactone), and combinations thereof. The gel may further comprise a chemical cross-linking agent having two or more reactive groups in order to form chemical bridges between two or more polymeric molecules. Examples of such cross-linking agents include diacrylates, oligoacrylates, dimethacrylates, oligomethacrylates, divinyl ethers, certain cations, and combinations thereof. Examples of materials that expand due to environmental stimuli include shape memory alloys and polymers, such as Nitinol™ or polyurethanes and poly(norbornene), which expand with changes in temperature.

Other expansive materials that respond to changes in moisture, ionic strength, temperature, pH, or materials that selectively absorb blood borne substances (e.g. silicones or other polymers which absorb lipids) may also be used. The rate at which the second coil 14 expands may be customized, such as by changing a composition of the second coil 14, so that placement and repositioning of the coil 10 may be performed within a period after it has been delivered to a site. The rate may also be controlled by a coating that may be soluble or insoluble which, in either case, limits diffusion of fluid into the second coil 14.

In the embodiment in FIGS. 1-3, the first and second coils 12, 14 are wound from first and second elongate bodies 20, 22, respectively. As discussed above, the first elongate body 20 can be a metal wire, e.g., a Pt/8% W (platinum/tungsten) wire. The second elongate body 22 may be made from a hydrogel. One or both of the first and second elongate bodies 20, 22 may be solid bodies, or formed from multiple filaments made of substantially non-expansile and expansile materials, respectively. The second elongate body 22 is configured to undergo a reaction that changes a structural characteristic when it is placed in a body cavity. The second elongate body 22 includes an expansible material, which will expand in size when placed in an aqueous environment within a living mammal. As shown in FIG. 3, the cross-section of the second elongate body 22 in this embodiment is configured such that it can expand from slightly smaller than the space 24 between first coil loops 16 to slightly larger than the space 24. In other embodiments, the cross-sectional dimension of the second elongate body 22 is configured such that its swollen cross-sectional dimension is at least equal to 100%-1,200% of the space 24 between first coil loops 16. As shown in FIG. 3, the expanded second elongate body 22 imparts axial or longitudinal stress within the coil 10 by compressing the first elongate body 20, to thereby increase hoop strength, and stiffen and stabilize the coil 10, in-situ. In this embodiment, hoop strength and coil stiffness and stability may be increased without exerting any radially directed force on the vaso-occlusive coil 10.

When the second elongate body is in a contracted state (FIGS. 1 and 2), the first and second elongate bodies 20, 22 have approximately the same outside diameter ("OD"). The bending moment of a coil is exponentially proportional to the diameter of the material from which it is wound, to the power of four. Consequently, when the second elongate body 22 is in the expanded state (FIG. 3), the vaso-occlusive coil 10 has non-uniform bending behavior along its length and more readily bends at the first coil loops 16 along its length. These bending points provide better conformability and packing performance.

While the first and second elongate bodies 20, 22 in the embodiment in FIGS. 1 and 2 have approximately the same OD when the second elongate body is in a contracted state, the elongate bodies from which the component coils are co-wound may have different ODs in other embodiments. The ODs of the first and second elongate bodies 20, 22 can be optimized based on the target application of the vaso-occlusive coil, i.e. framing, filling, or finishing. Larger ODs contribute to overall coil stiffness and smaller ODs lead to easier bending. The ratio of the first elongate body 20 OD to the second elongate body 22 OD can also be optimized based on the target application of the vaso-occlusive coil. In the vaso-occlusive coil 10 in FIG. 1, the first elongate body 20 and the second elongate body 22 (contracted) have an OD of approximately 0.0015 inches. The first and second elongate bodies 20, 22 are co-wound on a 0.007" mandrel.

Figure 4:
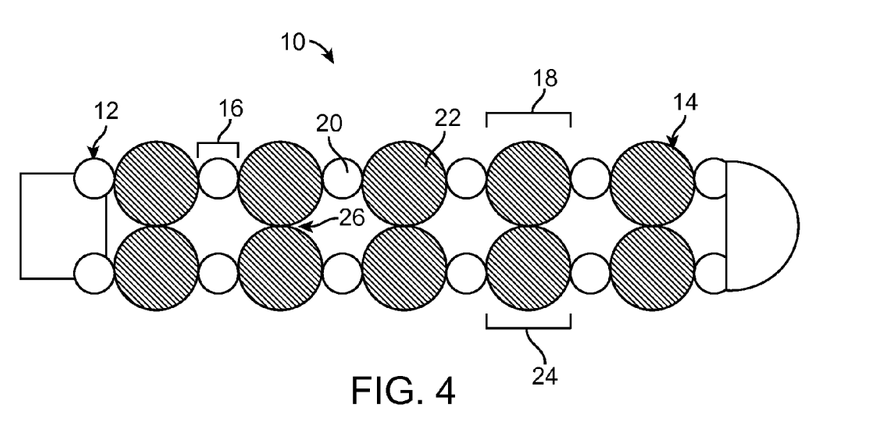
FIG. 4 is a detailed longitudinal cross-section view of a vaso-occlusive coil constructed according to another embodiment of the disclosed inventions, with the second elongate body in an expanded state.

The embodiment shown in FIG. 4 is similar to the one in FIGS. 1-3, except that it has a second elongate body 22 configured to expand until the lumen 26 formed by the second coil 14 and each second coil loop 18 is substantially closed by, or in direct contact with, the expanding second elongate body 22. Radially inward expansion of the second elongate body 22 imparts radial stress within the coil 10, in addition to the above-described axial or longitudinal stress, to further stiffen and stabilize the coil 10, in-situ. As also shown in FIG. 4, the expansion of the second elongate body 22 also increases the overall length of the vaso-occlusive coil 10 compared to the contracted state (FIG. 2).

Figure 5:
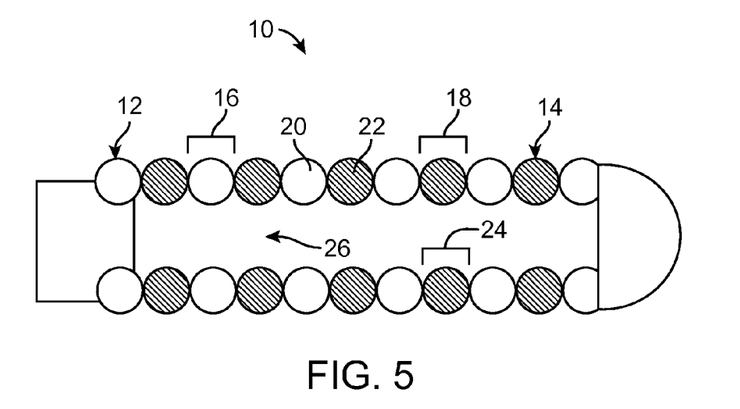
FIGS. 5 to 11 are detailed side views of vaso-occlusive coils according to respective embodiments of the disclosed inventions, with the second elongate body in a contracted state.
Figure 6:
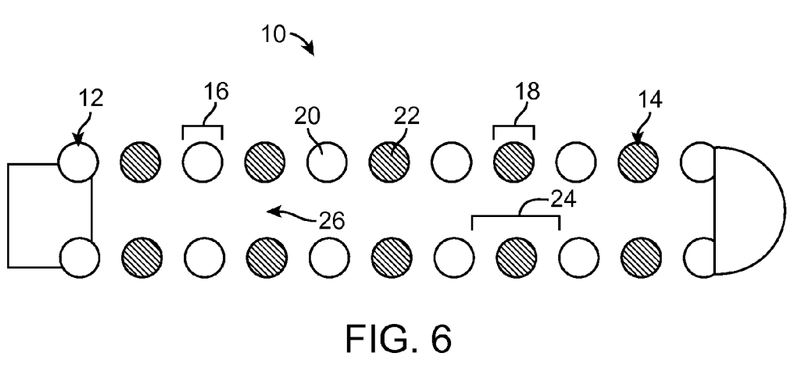

FIG. 5 illustrates a vaso-occlusive coil 10 where the diameter of the second elongate body 22, in its contracted state, is approximately the same size as the space 24 between first coil loops 16. When the second elongate body 22 expands in this embodiment, it exerts even more axial or longitudinal stress within the coil 10 than the embodiment in FIGS. 1-4. The embodiment in FIG. 6 has spaces 24 between first coil loops 16 that are larger than those in the embodiments in FIGS. 1-5 and substantially larger than the diameter of the second elongate body 22. Accordingly, when the second elongate body 22 expands in this embodiment, it exerts less axial or longitudinal stress within the coil 10 than the embodiments in FIGS. 1-5. However, the embodiment in FIG. 6 will exert radial stress when the second elongate body 22 expands sufficiently to substantially close the lumen 26 in the second coil 16 (FIG. 4).

Figure 7:
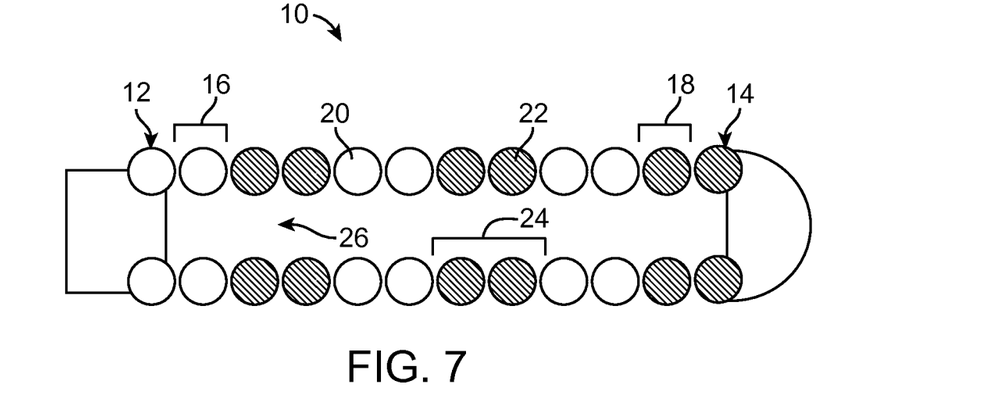
Figure 8:
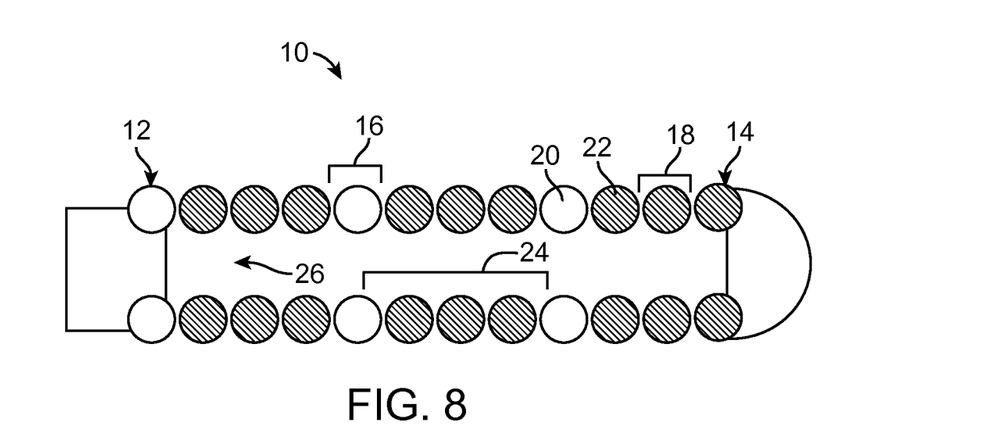
Figure 9:
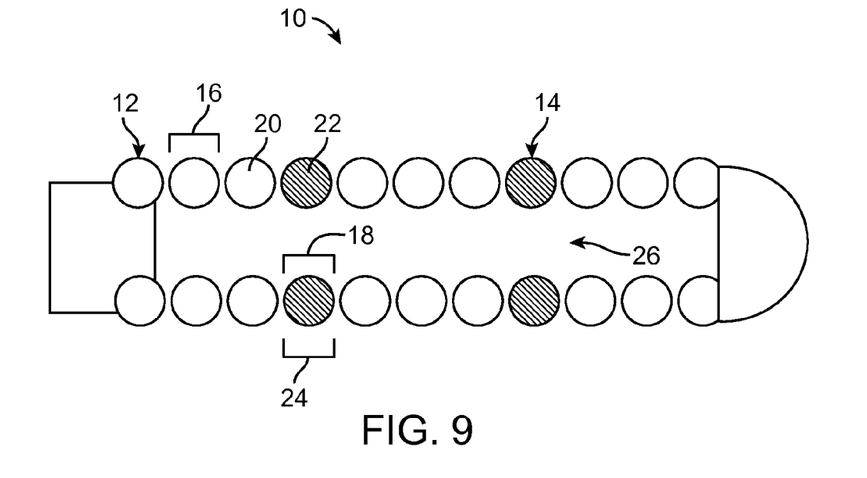
Figure 10:
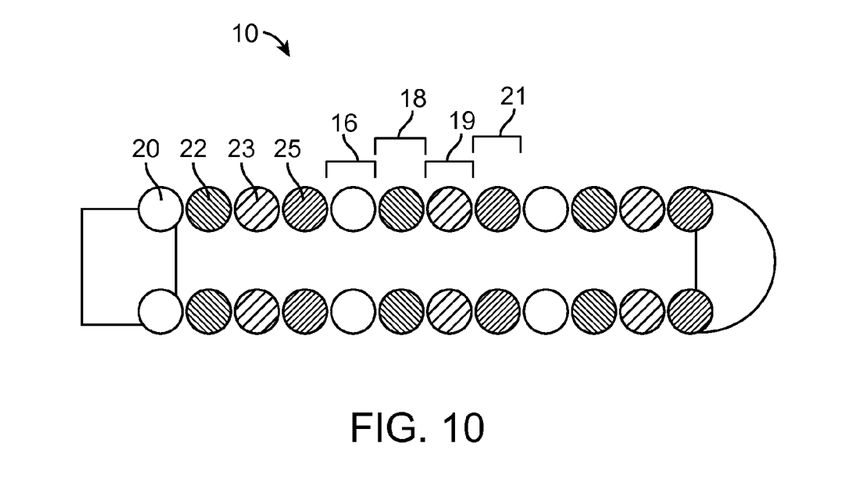

FIGS. 7-9 show various winding patterns that fall within the scope of the invention. While the embodiment in FIGS. 1-6 have alternating first and second coil loops 16, 18, any pattern of first and second coil loops may be produced by co-winding. The embodiment in FIG. 7 has alternating pairs of first and second coil loops 16, 18. The embodiment in FIG. 8 has triplets of second coil loops 18 separated single first coil loops 16. The embodiment in FIG. 9 has triplets of first coil loops 16 separated by single second coil loops 18. The embodiment in FIG. 10 is wound from first, second, third, and fourth elongate bodies 20, 22, 23, 25, which form a respective repeating series of first, second, third, and fourth loops 16, 18, 19, 21. The first and third elongate bodies 20, 23 can be a metal wire, e.g., a Pt/8% W (platinum/tungsten) wire. The second and fourth elongate bodies 22, 25 may be made from a hydrogel. The winding patterns in FIGS. 7-10 are exemplary and the invention includes all possible winding patterns.

Figure 11:
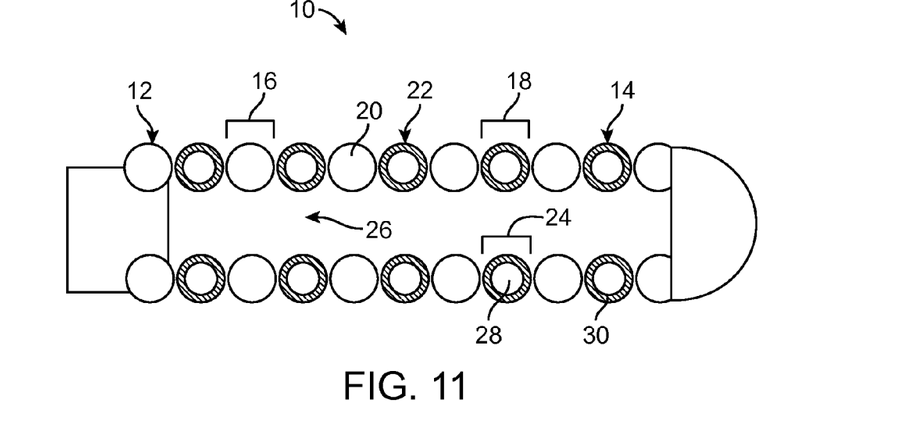

FIG. 11 shows another embodiment, wherein the second elongate body 22 is made from a core 28 of substantially non-expansile material covered by a coating 30 of expansile material. The construction of this second elongate body 22 allows it to be expansile while having increased stiffness from the non-expansile core 28. This second elongate body 22 expands when the coating 30 absorbs liquid.

In addition to the variations described above, the vaso-occlusive coils 10 of the disclosed inventions can be co-wound from elongate bodies that differ in other characteristics, as long as one of the first elongate bodies is non-expansile and a second one of the elongate bodies is expansile. For instance, the first and second elongate bodies 20, 22 may have different cross-sectional geometries, such as circular, oval, triangular, and square. More angular cross-sectional geometries form more discrete contact points between two adjacent loops, where the surface of at least one loop forms an acute angle. The more discrete contact points, in turn, result in easier bending when force is applied to the vaso-occlusive coil 10.

Further, the first and/or second elongate bodies 20, 22 may be formed from a pair of elongate members that are pre-twisted together before co-winding with the other elongate body. The pre-twisted pair of elongate members has a defined pitch. The resulting vaso-occlusive coil 10 has non-uniform bending behavior not only along its length, but also along its circumference. The vaso-occlusive coil 10 is more likely to bend at a loop made from the pre-twisted pair of elongate members, which each have a smaller OD than the other elongate body. The vaso-occlusive coil 10 is also more likely to bend along the short cross-sectional axis of the pre-twisted pair of elongate members where the moment of inertia or bending stiffness is lowest.

Moreover, the first and/or second elongate bodies 20, 22 may have flattened sections with a short cross-sectional axis. The vaso-occlusive coil 10 is more likely to bend where the short cross-sectional axis is perpendicular to the longitudinal axis of the vaso-occlusive coil 10.

The first and second elongate bodies 20, 22 forming the vaso-occlusive coils 10 of the disclosed inventions may differ from each other in any of the above-described characteristics or in any combination or sub-combination of the above-described characteristics.

In any of the embodiments described herein, the first elongate body 20 used to form the first coil 12 may have a cross-sectional dimension that is in the range of 0.00002 and 0.01 inches. The second elongate body 22 used to form the second coil 14 may have a cross-sectional dimension that is in the range of 0.00002 and 0.01 inches (non-expanded) and 0.000025 to 0.15 inches (expanded). The first coil 12 formed by the first elongate body 20 may have a cross-sectional dimension between 0.003 and 0.03 inches. The second coil 14 formed by the second elongate body 22 may have a cross-sectional dimension between 0.003 and 0.03 inches (non-expanded) and 0.0035 to 0.45 inches (expanded). For neurovascular applications, the diameter of the first and second coils 12, 14 may be anywhere from 0.008 to 0.025 inches, preferably from 0.009-0.015 inches, whether the second elongate body 22 is non-expanded or expanded. In other embodiments, the first and second elongate bodies 20, 22 may have other cross-sectional dimensions, and the first and second coils 12, 14 may have other cross-sectional dimensions. In some embodiments, the first and second elongate bodies 20, 22 for forming the first and second coils 12, 14 should have a sufficient diameter to provide a hoop strength, when the second elongate body 22 is expanded, to the resulting vaso-occlusive coil 10 sufficient to hold the coil 10 in place within the chosen body site, lumen or cavity, without substantially distending the wall of the site and without moving from the site as a result of the repetitive fluid pulsing found in the vascular system.

In any of the embodiments described herein, the axial length of the first and second coils 12, 14 may be in the range of 0.5 to 100 cm, and more preferably, in the range of 1.0 to 60 cm, whether the second elongate body 22 is non-expanded or expanded. Depending upon use, the first and second coils 12, 14 may have 10-75 turns per centimeter, or more preferably 10-40 turns per centimeter. In other embodiments, the first and second coils 12, 14 may have other lengths and/or other number of turns per centimeter.

Further, while the above-described embodiments of FIGS. 1-10 are directed to single layer coils, it should be appreciated by those skilled in the art that double-coil embodiments, i.e., having an outer coil layer and an inner coil layer may be included in alternative embodiments, in accordance with the inventive aspects disclosed herein.

Figure 12:
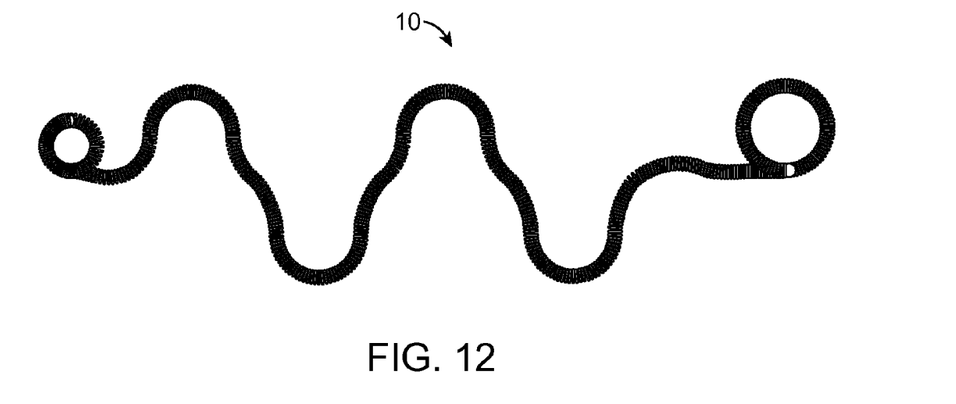
FIG. 12 is a perspective view of a vaso-occlusive coil in a natural state mode, illustrating one exemplary secondary configuration according to an embodiment of the disclosed inventions.

In some embodiments, the vaso-occlusive coils 10 described herein may have the simple linear shape shown previously, or may have shapes which are more complex. FIG. 12 shows what is termed a "secondary" shape in that it is formed from the primary coil by winding the primary coil on a form of a desired shape, e.g. a mandrel, and then heat treating the so-formed shape. Various other secondary shapes may be implemented in embodiments of the vaso-occlusive coil 10 described herein.

Although particular embodiments have been shown and described herein, it will be understood by those skilled in the art that they are not intended to limit the present inventions, and it will be obvious to those skilled in the art that various changes and modifications may be made (e.g., the dimensions of various parts) without departing from the scope of the disclosed inventions, which is to be defined only by the following claims and their equivalents. The specification and drawings are, accordingly, to be regarded in an illustrative rather than restrictive sense. The various embodiments shown and described herein are intended to cover alternatives, modifications, and equivalents of the disclosed inventions, which may be included within the scope of the appended claims.

What is claimed is:

1. A vaso-occlusive device, comprising:
   a first coil made from a first material wherein the first coil forms first coil loops; and
   a second coil forming second coil loops at least partially co-wound with the first coil loops and made from a second material, wherein the first material is substantially non-expansile and the second material is expansile.

2. The vaso-occlusive device of claim 1, wherein the first material is a metal.

3. The vaso-occlusive device of claim 2, wherein the first material is selected from the group consisting of platinum, platinum-tungsten alloy, platinum-iridium alloy, platinum rhenium alloy, and platinum palladium alloy.

4. The vaso-occlusive device of claim 1, wherein the second material is a polymer.

5. The vaso-occlusive device of claim 4, wherein the second material is a hydrogel.

6. The vaso-occlusive device of claim 1, wherein the first coil loops and the second coil loops are packed together such that each loop is in contact with loops adjacent thereto.

7. The vaso-occlusive device of claim 1, further comprising spaces disposed between at least some of the first coil loops and respective adjacent second coil loops.

8. The vaso-occlusive device of claim 1, wherein the first and second coils are co-wound such that a plurality of successive first coil loops separate an adjacent pair of second coil loops.

9. The vaso-occlusive device of claim 1, wherein the first and second coils are co-wound such that a plurality of successive second coil loops separate an adjacent pair of first coil loops.

10. The vaso-occlusive device of claim 1, wherein the first and second coils are co-wound such that a plurality of successive first coil loops are adjacent a plurality of successive second coil loops.

11. The vaso-occlusive device of claim 1, wherein the second coil has a contracted state and an expanded state.

12. The vaso-occlusive device of claim 11, wherein the second coil expands radially in its expanded state.

13. The vaso-occlusive device of claim 11, wherein the second coil and the vaso-occlusive device both expand longitudinally when the second coil is in its expanded state.

14. The vaso-occlusive device of claim 11, wherein the second coil transitions from its contracted state to its expanded state when it absorbs liquid.

15. The vaso-occlusive device of claim 11, wherein, when the second coil is in its expanded state, the second coil loops compress the first coil loops.

16. The vaso-occlusive device of claim 11, the second coil defining an axial lumen, wherein, when the second coil is in its expanded state, the second coil loops substantially close the lumen.

17. The vaso-occlusive device of claim 11, wherein the vaso-occlusive device has increased stiffness when the second coil is in its expanded state.

18. The vaso-occlusive device of claim 1, further comprising third and fourth coils at least partially co-wound with the first and second coils.

19. The vaso-occlusive device of claim 1, wherein the first coil loops and the second coil loops are collated together.

20. A vaso-occlusive device, comprising:
   a first coil forming first coil loops and made from a first material; and
   a second coil forming second coil loops and at least partially co-wound with the first coil loops and made from a second material coated with a third material, wherein the first and second materials are substantially non-expansile and the third material is expansile.

* * * * *